US005948956A

United States Patent [19]
Lee et al.

[11] Patent Number: 5,948,956
[45] Date of Patent: Sep. 7, 1999

[54] TRANSGENIC PLANTS AND METHOD FOR NODE SEGMENT TRANSFORMATION

[75] Inventors: Lisa Lee, Marysville; John Bradley Berg, Columbus, both of Ohio

[73] Assignee: OMS Investments, Inc., Wilmington, Del.

[21] Appl. No.: 08/951,994

[22] Filed: Oct. 16, 1997

[51] Int. Cl.$^6$ .............................. C12N 15/82; C12N 5/04; A01H 4/00; A01H 5/10
[52] U.S. Cl. .......................... 800/320; 435/469; 435/468; 435/410; 435/419; 435/421; 435/430; 435/252.3; 800/278; 800/293; 800/298; 800/320
[58] Field of Search .............................. 435/172.3, 252.2, 435/418, 469, 468, 410, 419, 421, 430, 252.3; 800/205, 250, DIG. 74, DIG. 55, 278, 293, 295, 298, 320

[56] References Cited

U.S. PATENT DOCUMENTS 5,240,839  8/1993  Serres et al. .

FOREIGN PATENT DOCUMENTS 0 424 047   4/1991   European Pat. Off. .
WO 96/22015 7/1996   WIPO .

OTHER PUBLICATIONS

Beard, James B. (1973). Turfgrass: Science and Culture. Prentice–Hall, Inc., Englewood Cliffs, NJ, pp. 23–53.
Darnell, J., H. Lodish, and D. Baltimore (1990). Molecular Cell Biology, Second Edition. Scientific American Books, Inc., pp. 175–176.
Esau, Katherine (1965). Plant Anatomy, Second Edition. John Wiley & Sons, New York, p. 73.
Hartman, C.L., et al. (1994). Herbicide resistant turfgrass (*Agrostis palustris*) by biolistic transformation. Bio/Technology 12: 919–923.
Klein, Theodore, M., et al. (1988). Stable genetic transformation of intact Nicotiana cells by the particle bombardment process. PNAS 85: 8502–8505.
Kuo, Yu–Jen and M.A.L. Smith (1993). Plant regeneration from St. Augustinegrass immature embryo–derived callus. Crop Sci. 33: 1394–1396.
Lee, Lisa (1996). Turfgrass biotechnology. Plant Science 115: 1–8.
Alexandrova, P.D. et al. (1996). Micropropagation of Switchgrass By Node Culture. Crop Sci. 36: 1709–1711.
Mauseth, James D. (1991). Botany: An Introduction to Plant Biology. Saunders College Publishing, Orlando.
Pérez–Vicente, R., et al. (1993). Culture of vegetative and floral meristems in ryegrasses: potential targets for microballistic transformation. J. Plant Physiol. 142: 610–617.
Sanford, J.C., et al. (1993). Optimizing the biolistic process for different biological applications. Methods in Enzymology 217: 483–509.
Tomes, Dwight T., et al. (1990). Transgenic tobacco plants and their progeny derived by microprojectile bombardment of tobacco leaves. Plant Molecular Biology 14: 261–268.
Youngner, V.B. (1969). Turfgrass Science. American Society of Agronomy, Inc., Madison, WI, pp. 187–216.
Zhong, H. et al. Transgenic plants of turfgrass (*Agrostis palustris* Huds.) from microprojectile bombardment of embryogenic callus. *Plant Cell Reports*. 1993, vol. 13, pp. 1–6.
Zaghmout and Torello. Journal of Plant Physiology. 1992. vol. 140: 101–105. (Abstract enclosed from Biosis).
Dalton and Thomas Journal of experimental of Botany. 1994. supplement. 45. p. 58.
Matzke and Matzke. Plant Physiology. 1995. 107: 679–685.
Finnegan and McElory. Bio/Technology. 1994. vol. 12: 883–888.
Napoli et al. The Plant Cell. 1989. vol. 2: 278–289.
Hartman et al. Bio/Technology. 1994. vol. 12: 919–923.
El'Konin et al. Biosis search database: 85229357. 1984 (Translation from Russian).
Alexandrova et al. Crop Science. 1996. vol. 36: 175–178.

*Primary Examiner*—Elizabeth F. McElwain
*Assistant Examiner*—Ousama M-Faiz Zaghmout
*Attorney, Agent, or Firm*—Jones, Day, Reavis & Pogue

[57] ABSTRACT

Transgenic monocotyledonous plants are produced by inserting a foreign genetic material directly into a node segment of a stem of a plant and thereafter subjecting the node segment to conditions sufficient to permit regeneration of the node segment into a plantlet. Preferably, the genetic material is inserted by biolistic transformation, Agrobacterium, or direct DNA uptake mediated by electroporation. The process is especially useful for producing transgenic ryegrasses, fescues and turfgrasses, such as St. Augustinegrass, creeping bentgrass, Kentucky bluegrass, and the like.

36 Claims, 4 Drawing Sheets

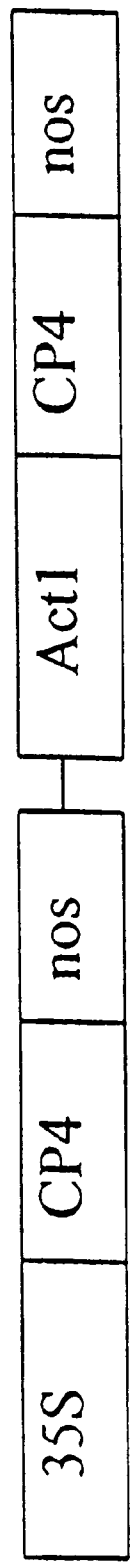
FIG.4

TRANSGENIC PLANTS AND METHOD FOR NODE SEGMENT TRANSFORMATION

BACKGROUND OF THE INVENTION

The invention relates generally to the genetic transformation of plants and, more particularly, to a method for producing a transgenic monocotyledonous plant by introducing foreign genetic material directly into a node segment of a non-transgenic plant and then regenerating and selecting for a transgenic plant. Publications referred to in this specification are alphabetically listed at the end of the description.

The agriculture industry has benefitted from recent advances in the field of biotechnology that have enabled the development of hardier varieties of plants for crop improvement and ornamental purposes. In particular, the use of sophisticated recombinant DNA techniques has resulted in the production of genetically improved monocotyledonous grass cultivars, including cereal crops, forage grasses and turfgrasses, and dicotyledonous cultivars, such as tobacco, having increased yields, herbicide resistance, disease resistance, pest resistance, stress tolerance, durability, and the like.

The importance of improved cereal crops (e.g. maize, wheat, rice, barley) and forage grasses, such as ryegrasses (Lolium ssp.), orchardgrasses (Dactylis ssp.) and fescues (Festuca ssp.), is well recognized. Turfgrasses are important for providing attractive ground cover, such as for residential lawns, and for providing a support for many recreational sports, such as baseball, soccer and golf. The maintenance of golf courses, for example, requires intensive turfgrass management programs, including pesticide and herbicide treatments to prevent diseases and remove unwanted weed grasses. Therefore, production of turfgrasses that are herbicide-resistant and disease-resistant is beneficial to the turfgrass industry. The turfgrass seed market is second only to that of hybrid seed corn in being the largest seed market in the US.

Monocotyledons are generally recalcitrant to manipulation in vitro and to genetic transformation. Although transfer of foreign genes into plants by infection with Agrobacterium tumefaciens containing plasmid DNA is routine for many dicotyledons that readily form callus after wounding, the procedure is not routinely applicable in monocotyledons in which callus formation and transformation is more difficult. In addition to Agrobacterium, two other conventional methods of gene delivery, protoplast transformation and biolistic transformation, have been used to produce transgenic monocotyledonous and dicotyledonous plants.

Until the present invention, regenerable embryogenic tissue cultures have provided the major resource for the genetic transformation of monocotyledons. For example, mature seeds have been commonly used to initiate embryogenic callus cultures to establish suspension cell cultures of cereals, forage grasses and turfgrasses. However, genotypic variation in outbreeding species, such as common ryegrasses, has been problematic because each seed-derived embryo possesses a unique genotype and it has been shown that standard culture conditions to induce embryogenesis are not optimal for every genotype. Therefore, embryogenic and suspension cell cultures from various sources have had to be selectively established on a species to species and genotype to genotype basis. Immature embryos and inflorescences have been used for callus initiation with pearl millet (Pennisetum americanum), Guinea Grass (Panicum maximum Jacq.), Napier Grass (Pennisetum purpureum Schum.) and perennial ryegrass (Lolium perenne). Basal sections of leaves have been used for callus initiation of orchardgrass (Dactylis glomerata L.) and tall fescue (Festuca arundinacea Schreb.). Chopped mature embryos have been used directly to establish suspension cultures of tall fescue, perennial ryegrass and Italian ryegrass (Lolium multiflorum); and both immature caryopses and mature seeds have been used to obtain embryogenic suspension cultures of Italian ryegrass and tall fescue (Lee, 1996). Regeneration of fertile plants has been obtained from isolated vegetative meristems of Italian ryegrass and perennial ryegrass (Pérez-Vicente et al., 1993), from shoot apex explants from foxtail millet (Setaria italica L.), and from suspension culture-derived protoplasts of meadow fescue (Festuca pratensis Huds.). Switchgrass (Panicum virgatum L.) plants have been micropropagated from axillary buds in node segments in tissue culture, but there are no reports of transformation (Alexandrova et al., 1993).

Stable transformed callus lines and transgenic plants from callus of perennial ryegrass have been established. Transformed callus lines of Italian ryegrass have also been reported but transgenic plants have not been regenerable from these callus lines. Kentucky bluegrass (Poa pratensis L.) plants can be regenerated from protoplasts, embryogenic suspension cultures and seed-derived callus cultures, but there are no reports of transformation. Until the present invention, there have also been no reports of transformation of St. Augustinegrass (Stenotaphrum secundatum [Walt] Kuntze), although plants have been regenerated from immature embryo-derived callus (Kuo et al., 1993).

Protoplast transformation has been used to obtain transgenic turfgrasses, including orchardgrass, tall fescue, creeping bentgrass, redtop and red fescue. Direct DNA uptake by the protoplasts was enhanced by the use of polyethylene glycol (PEG) or electroporation. However, protoplast transformation has only been successful in a few cultivars of cereal crops and regeneration of cereal plants from protoplasts appears to be strongly genotype and culture condition dependent. Moreover, for regeneration of turfgrass protoplasts, nurse cells in the protoplast cultures are required. These have reportedly been provided by addition to the culture of agarose beads with adhered cultured nurse cells or by a nurse cell feeder layer (Lee, 1996).

Microprojectile (biolistic) bombardment has been used successfully to produce transgenic turfgrass, such as creeping bentgrass (Hartman, et al., 1994), perennial ryegrass, tall fescue and red fescue, from embryogenic callus and suspension cultures. Biolistic bombardment employs high velocity metal particles to deliver biologically active DNA into plant cells. The concept was first described by Klein et al. (1987) and has become a successful DNA delivery method in a number of plants. An advantage of biolistic transformation is that a variety of recipient cell types can be used, including embryogenic callus, suspension cell cultures, immature or even mature embryos. For those monocotyledonous species and cultivars that form embryogenic cultures, but a protoplast regeneration system is not easy to establish, biolistic genetic transfer is a possible alternative method for cell transformation.

Successful genetic transformation of dicotyledonous plants, particularly tobacco plants, have been reported. Transgenic callus cell lines of tobacco have been recovered after microprojectile bombardment of tobacco leaves (Tomes, et al.) and suspension cell cultures (Klein et al., 1988) and transgenic tobacco plants were regenerated after biolistic bombardment of tobacco leaves. There have also been reports of successful transformation of chloroplasts of tobacco using the biolistic process.

Transformation of dicotyledonous sunflower and soybean cells from a cotyledonary node associated with an apical meristem has been reported. However, successful transformation required tissue culture of the node cells in the presence of a cytokinin, prior to transformation, to induce the cells to differentiate into meristematic tissue cells and to become synchronized in the cell cycle (Tomes et al., 1991).

Transgenic perennial fruit plants (dicotyledons), such as cranberry, have been obtained from transformed stem tissue after biolistic bombardment. However, successful transformation of the stem tissue required prolonged tissue culture in the presence of a cytokinin, prior to bombardment, to induce the formation of adventitious buds (Serres et al., 1993).

Transformation efficiencies (the ratio of the number of cells transformed to the number of starting cells) are low, however, for each of the above-described transformation methods, being on the order of $10^{-3}$ to $10^{-6}$.

In addition to the commonly used transformation techniques, available alternative methods for the direct introduction of foreign DNA into cells include silicon carbide fibers, electroporation of intact tissues, electrophoresis and microinjection. However, the stable expression of foreign genes, using these techniques, has yet to be established.

In view of the foregoing uncertainties and, in many cases, unreliability of current methods for successful transformation and regeneration of transgenic plants, there is a need for an efficient method of genetic transformation and regeneration that can be successfully applied to monocotyledonous plants, and particularly to turfgrasses, to obtain transgenic plants. Moreover, there is a need for a method of transforming monocotyledon plant cells that does not require extensive cell culture preparation and/or callus formation and/or extended tissue culture. Further, there is a need for improved techniques for genetic transformation and plant regeneration and selection systems for monocotyledons that allow introduction of foreign genetic material that alters the physical, biochemical and/or physiological properties of the plant to provide beneficial traits or reduce unwanted characteristics.

SUMMARY OF THE INVENTION

The invention provides a simple and efficient process for producing a transgenic monocotyledonous plant by inserting a foreign genetic material directly into a node segment of a stem of a plant and thereafter subjecting the node segment to culture conditions sufficient to permit regeneration of the node segment into a plantlet. As used in the context of the invention, the term "node segment" includes any joint in a stem from where one or more leaves may grow and also includes any lateral (axillary) buds on the side of the stem, as in a leaf axil. The definition further includes node segments occurring in specialized stems known to those skilled in the art, such as rhizomes, stolons, tubers, bulbs, corms, cladophylls, and in stems modified with spines or tendrils. Preferably, the node segment is associated with an intercalary meristem. By direct transfer of the genetic material into node segment tissue, the process of the invention eliminates the extensive cell preparation, tissue dissection, and/or extended period in tissue culture required by previous transformation methods using embryonic cell or callus cultures, protoplasts or suspension cell cultures.

It has been discovered that in vitro regeneration of transgenic shoots from transformed node segment tissue does not require callus formation, at least in certain turfgrasses such as St. Augustinegrass. Therefore, the time period required for regeneration of transgenic plantlets from transformed node segment cells is greatly reduced in comparison to regeneration systems requiring callus formation.

The genetic material may be inserted into the node segment by any method of genetic transfer, such as those described above, but preferably is inserted by biolistic (microprojectile) bombardment, by transfer mediated by Agrobacterium, or by direct DNA uptake mediated by electroporation.

The process may be used to transform any plant that has a stem having at least one node segment. Therefore, the process may be used for monocotyledonous plants including, but not limited to cereal crops, forage grasses, turfgrasses, herbs, woody plants, vegetable plants and flowering plants. The process is particularly preferred for producing transgenic grasses, especially turfgrasses and other grasses that can be vegetatively propagated, such as St. Augustinegrasses, bluegrasses, bentgrasses, bermudagrasses, buffalograsses, redtop, bahiagrasses, centipedegrass, zoysiagrasses, ryegrasses, fescues, and the like. Preferably, the node segments are associated with intercalary meristems.

By the process of the invention, transgenic plants may be produced that have one or more stable altered properties compared to a plant of the same species that is not transgenic for the property. Altered properties may be physical, biochemical or physiological in nature and include, but are not limited to, herbicide resistance, disease resistance, insect resistance, an improved nutritional content, expression of a pigment or a fragrance, and the like.

BRIEF DESCRIPTION OF THE DRAWINGS

FIG. 4 is a schematic illustration of three chimeric plasmids used for transforming St. Augustinegrass for herbicide resistance.

DETAILED DESCRIPTION OF THE INVENTION

In one embodiment, the invention concerns producing a transgenic plant from a genetically transformed node segment from a stem of a plant. Genetic transformation, according to the invention, is the stable integration of a foreign DNA into the genome of a plant cell, and includes integration of the foreign DNA into host cell nuclear DNA and/or extranuclear DNA in organelles (e.g. chloroplasts, mitochondria). The plant to be transformed may be a non-transgenic plant, or may be a plant that is already transgenic but comprises one or more foreign genes that are different than the new foreign gene or genes to be introduced. Foreign DNA is genetic material that is not indigenous to (not normally resident in) the plant before transformation or is not normally present in more than one copy. However, "foreign" DNA may include a further copy of an indigenous gene or genetic sequence that is introduced for purposes of co-suppression.

The foreign genetic material may comprise DNA from any origin including, but not limited to, plants, bacteria, viruses, bacteriophage, plasmids, plastids, mammals and synthetic DNA constructs. The DNA may be in circular or linear form and may be single-stranded or double-stranded. The DNA may be inserted into the host plant DNA in a sense or anti-sense configuration and in single-stranded or double-stranded form. All or part of the DNA inserted into the plant cell may be integrated into the genome of the host.

The node segment, according to the invention, may be obtained from a stem of any monocotyledonous plant that has at least one node. As described above, as used in the context of the invention, the term "node segment" includes any joint in a stem from where one or more leaves may grow and also includes any lateral (axillary) buds on the side of the stem, such as those occurring in a leaf axil. The part of the stem between two nodes is termed the "internode". Elongation of the stem occurs at the apex of the stem (apical meristem) and in the internode regions (intercalary meristems). The term "node segment", as used in the context of the invention, preferably includes portions of internode regions which include intercalary meristems. The definition of "node segment" further includes node segments occurring in rhizomes, stolons, tubers, bulbs, corms, cladophylls, and in stems modified with spines or tendrils.

Figure 1:
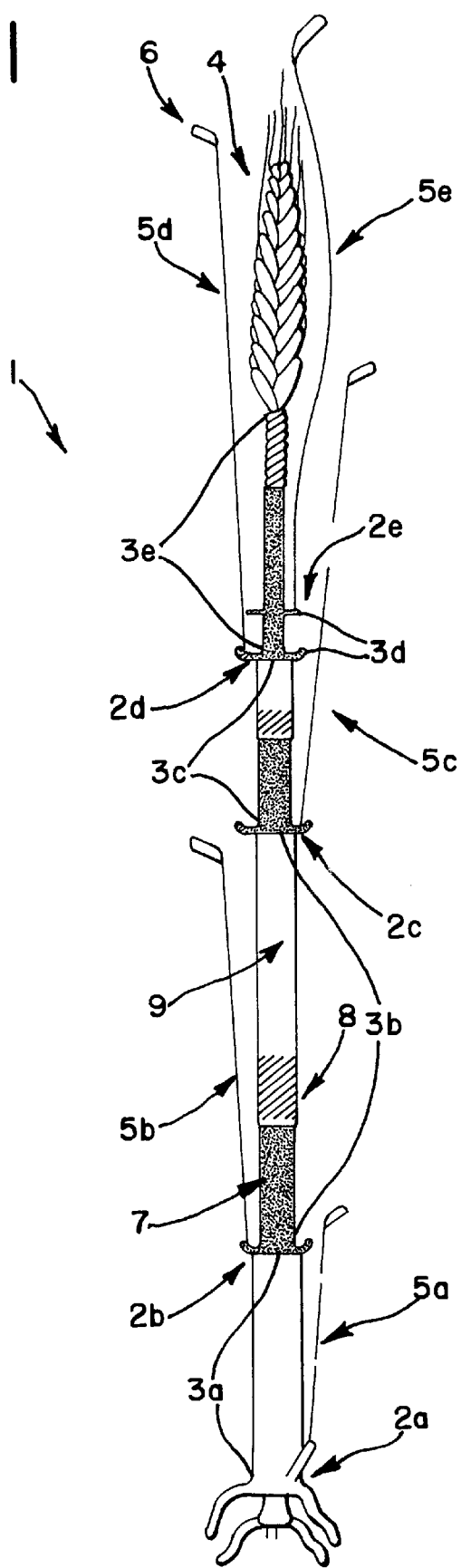
FIG. 1 is a schematic illustration of a rye plant showing node, internode and intercalary meristem regions.

Examples of node segments suitable for use in the invention are illustrated FIG. 1, adapted from a published figure (Esau, 1965). The illustrated plant 1 is a rye plant having five nodes 2a, 2b, 2c, 2d and 2e, five internodes 3a, 3b, 3c, 3d and 3e, and a spike 4. Leaf sheaths 5a, 5b, 5c, 5d and 5e extend upward from each node and terminate where leaf blades 6 diverge from them. The youngest tissue (intercalary meristems) 7 in the internodes 5b–5e is represented in black, somewhat older tissue 8 is hatched, and the most mature tissue 9 is white.

A node segment of the invention is a tissue excised from a plant stem, such as that illustrated in FIG. 1, comprises at least one node and may include internode tissue from above and below the node. A suitable node segment, as illustrated in FIG. 1, could contain one or more of nodes 2a–2e. The tissue above the node in the node segment may comprise the youngest tissue 7 and somewhat older tissue 8. Preferably the tissue above the node comprises the youngest intercalary meristem tissue 7. However, older intercalary meristem tissue may also be used because it is known that the meristematic activity in the region of the nodes can be reactivated even in mature stems. The tissue below the node in the node segment may comprise any or all of the tissue contained in the internode below the node of interest.

Figure 2:
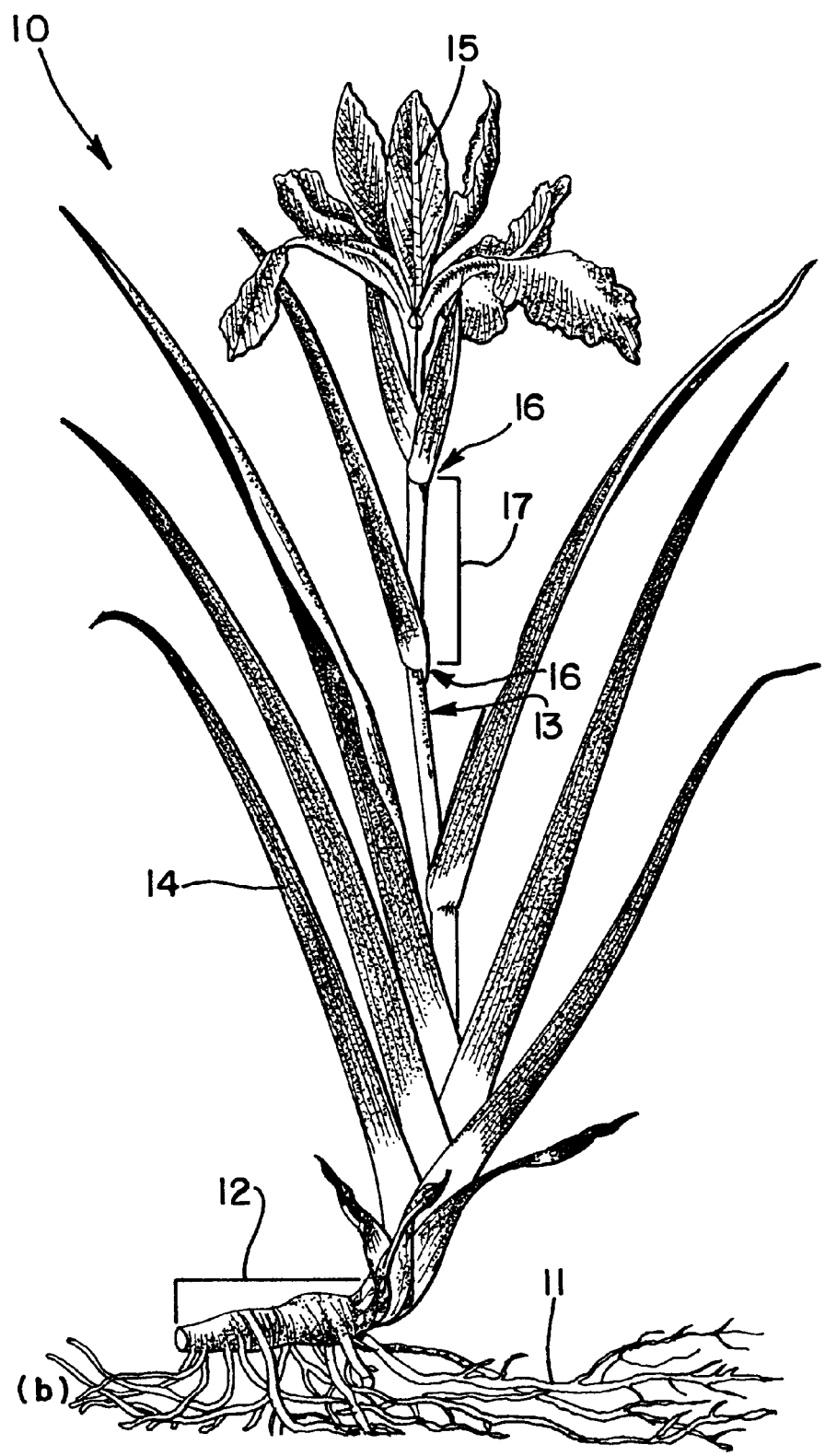
FIG. 2 is a schematic illustration of an herbaceous monocotyledonous plant showing nodes, internodes and a rhizome.

FIG. 2 illustrates an herbaceous monocotyledon 10 (an iris), suitable for use in the invention, consisting of roots 11, rhizome 12, stem 13, leaves 14 and flower 15. Nodes 16 and internodes 17 occur on the stem 13. The rhizome 12 is a specialized horizontal stem that grows below ground. The illustrated roots 11 are adventitious roots growing from the rhizome (stem). The rhizome 12 has scalelike leaves and lateral buds at each node, with short to long internodes between the nodes.

The plant according to the invention includes any plant having a stem with at least one node, preferably associated with an intercalary meristem, and includes any plant so defined in the group Monocotyledoneae including, but not limited to, any plant falling within the major families and subfamilies, including Bambosoideae which includes bamboo, Arundinoideae which includes pampas grass and reeds, Pooideae, which includes oats, barley, rye, wheat, maize, corn, Phalaenopsis, Poaceae which includes the Festucoideae, namely Chlorideae, including millet, tef, Mitchell grass, Rhodes grass, bermudagrass, buffalograsses, Kallar grass and gramas, Hordeae, including wheatgrasses and ryegrasses, Zoysieae, including zoysiagrasses, Agrostideae, including bentgrasses, redtop, beachgrasses and timothys, Festuceae, including bromegrasses, fescues and bluegrasses, and the Panicoideae, which includes St. Augustinegrasses, sorghum, maize, surinamgrass, pangolagrass, sugar cane, vetivergrass, carpetgrasses, bahiagrasses and kikuyugrasses.

The plants suitable for use in the invention may be annual, biennial or perennial plants. Most preferably, the plant of the invention is any monocotyledonous plant that can be vegetatively propagated from a node segment to form a shoot and root system. For example, dumb cane (*Dieffenbachia maculata*) and asparagus (*Asparagus officinalis*) can be propagated from lateral buds and Phalaenopsis can be propagated from nodal sections.

In a preferred embodiment of the invention, the transforming DNA comprises one or more genes or partial genes that code for expression of an altered physical, biochemical or physiological property of the transgenic plant, compared with a plant of the same species that is not transgenic for the same property, to provide a beneficial trait or reduce an unwanted characteristic. Examples of characteristics that may be altered by genetic transformation include, but are not limited to, herbicide resistance, disease resistance, insect resistance, drought resistance, dwarfism, improved nutrient utilization, antibiotic resistance, expression of a pigment, expression of a fragrance, improved nutritional content, increased production of seed, increased production of fruit, increased stress tolerance, expression of a regulatory gene to control indigenous genes, reduction of allergenic pollen production, and the like, and combinations of any of the foregoing.

The genetic techniques of the invention also contemplate modified plants having indigenous genetic sequences deleted or otherwise mutated.

Examples of genes that may be integrated into the host genome to produce a stable expression of an altered characteristic include, but are not limited to, the bar gene which confers the ability to detoxify bialaphos and the neomycin phosphotransferase II gene (NPTII) which confers resistance to the antibiotic kanamycin.

A process for producing a transgenic plant according to the invention comprises providing a node segment from a stem of a plant, inserting a foreign genetic material into the node segment, and subjecting the node segment to conditions sufficient to permit regeneration of the node segment into a new stably transformed plantlet.

Any method of introducing DNA into the cell of the node segment may be used in the invention including, but not limited to biolistic bombardment with DNA-coated microprojectiles, Agrobacterium-mediated delivery and direct DNA uptake mediated by electroporation, polyethylene glycol (PEG), silicon carbide fibers, electrophoresis or microinjection. The preferred techniques for delivering the DNA are biolistic bombardment, Agrobacterium, and direct uptake of DNA mediated by electroporation.

Although several methods for direct DNA delivery are known, preferably the DNA is delivered into the host cell by a transforming or cloning vector, such as plasmid. Selection and/or synthetic construction of plasmids containing specific genes are well known in the art. Synthetic constructs of chimeric plasmids contain the gene or gene of interest and frequently comprise promoter and/or leader sequences obtained from diverse sources to facilitate insertion into the host genome. Examples of plasmids commonly used to transform plant cells include, but are not limited to, Ti plasmids (*Agrobacterium tumefaciens*) (Darnell, Lodish and Baltimore, 1990), a plasmid containing a β-glucuronidase gene (GUS) and/or a NPTII gene and a cauliflower mosaic virus (CaMV) promoter plus a leader sequence from alfalfa mosaic virus (Sanford et al., 1993), a plasmid containing a bar gene cloned downstream from a CaMV 35S promoter and a tobacco mosaic virus (TMV) leader. Other plasmids may additionally contain introns, such as that derived from alcohol dehydrogenase (adhI), or other DNA sequences. The size of the vector is not a limiting factor. For example, intact bacterial cells (e.g. *Escherichia coli*) containing or transformed to contain a gene of interest can be delivered as biolistic projectiles.

The successful delivery of the DNA into a cell may be preliminarily evaluated by the transient expression of a "reporter" gene. A reporter gene is a component of the DNA used for transformation and may be the same as or different than the gene conferring another desired property. The property conferred on the transformed cell or tissue by the reporter gene is usually easily detectable. "Transient expression" denotes the expression, often cytoplasmic, of a gene before the gene has been stably integrated into the genome of the treated cells or tissue. For example, commonly used reporter genes are genes coding for the production of chloramphenicol acetyltransferase or neomycin phosphotransferase, which confer resistance to the antibiotics chloramphenicol and kanamycin, respectively, or the *E. coli* β-glucuronidase gene (gusA), the products of which can be detected by a histochemical assay. Genes conferring herbicide resistance can also be used as reporter genes. In this case, cells or tissues may be tested for transient expression of the genes by culture in the presence of the herbicide. Shoots or plantlets growing in the presence of the herbicide are presumptively transformed. Confirmation of the integration of the gene into the genome of the host may be later confirmed by herbicide treatment of the resulting plants.

The node segment of the plant to be transformed is preferably cleared of any attached leaves prior to the transformation process. The tissue of the node segment is then trimmed to a desired size, preferably leaving a small amount of intercalary meristem tissue above the node. The foreign genetic material is preferably inserted into the node segment within about 48 hours of harvesting the node from the plant to minimize the possibility of shoot formation prior to transformation of the node segment. The node segment is placed in a Petri dish or other container containing a culture medium described further below prior to transformation.

An embodiment of the invention will now be described with respect to the transformation of turfgrasses, such as St. Augustinegrass, Kentucky bluegrass, creeping bentgrass, and the like, by biolistic transformation. However, as stated above, other transformation techniques may be employed and the invention methods may also be applied to other monocotyledonous plants. The method of the invention is particularly advantageous for transformation of turfgrasses and other monocotyledons that can be vegetatively propagated.

Figure 3A:
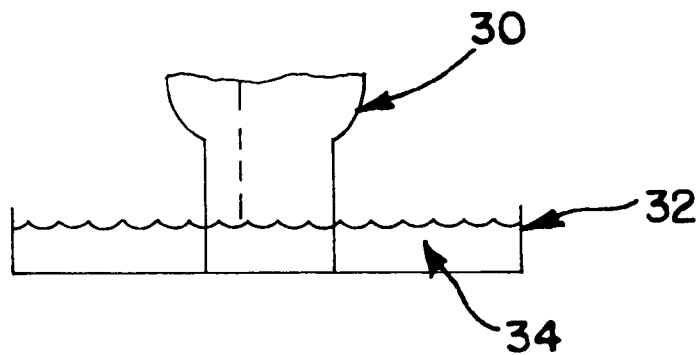
FIG. 3 is a schematic illustration of node segments having one, two or three vertical cuts in preparation for biolistic bombardment.
Figure 3B:
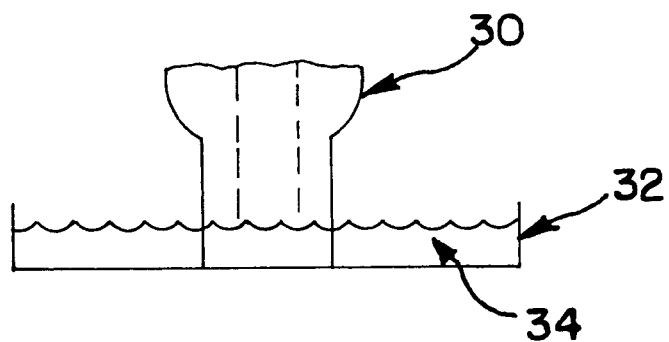
Figure 3C:
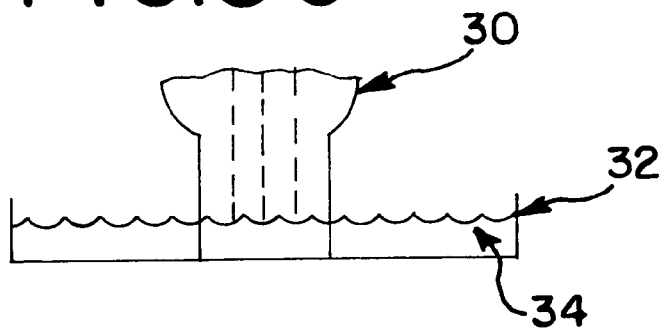

In one embodiment of the invention, illustrated in FIGS. 3A, 3B and 3C, if the node segment has a sufficient cross-sectional area, it may be useful to make a number of vertical cuts (dotted lines), preferably one to three, into the node segment 30, shown in Petri dish 32 containing culture medium 34, in order to increase the area exposed to the transformation vector. Alternatively, the node segments may remain uncut (not shown).

In another embodiment of the invention, callus formation may be induced in node segments having vertical cuts by culturing the node segments on a callus induction medium based on that of Murashige and Skoog (MS medium) containing a biologically active hormone, 2,4-dichlorophenoxyacetic acid (2,4-D), in a range from about 1 to about 10 mg/L, preferably about 5 mg/L, L-asparagine (about 50 mg/L to about 75 mg/L) or an equivalent amino acid or chemical entity, preferably thiamine HCl (about 0.05 mg/L to about 5 mg/L) or equivalent. The medium may also contain MS medium minerals and/or potassium iodide or equivalent or functional analogue at 0.83 mg/L. Culture conditions of temperature and light for callus formation are known to those skilled in the art.

In a preferred embodiment, callus formation is not induced in the node segments prior to bombardment. The node segments are placed in MS medium that does not contain a callus inducing hormone, such as 2,4-D, and callus formation is prevented. The node segments are then bombarded directly. A particular advantage of this embodiment of the invention is elimination of the tissue culture callusing time, which can take from 1 to 10 weeks for some monocotyledons. Callus formation is not necessary for regeneration of node segments from, for example, St. Augustinegrass.

The addition of an osmoticum (i.e., a supplemental agent increasing osmolarity) to the culture/bombardment medium may dramatically increase the rate of transformation, although the optimum concentration for each plant species varies. Elevated osmoticum concentrations are thought to protect the cells from leakage or bursting and may also improve particle penetration. Suitable osmotica, such as mannitol, sorbitol and mixtures of these, are known by those skilled in the art. Osmoticum concentrations in MS medium containing asparagine (MSA medium), of zero to 0.1M mannitol/0.1M sorbitol to 0.3M mannitol/0.3M sorbitol are suitable for culture/bombardment of turfgrasses, such as St. Augustinegrass.

The microprojectiles for bombardment of the node segments are preferably tungsten or gold, although other particles are known in the art (Sanford et al., 1993). Techniques for assessing the efficacy of the particle type are known in the art and are not herein described. Preferably, for turfgrasses, gold particles are employed, as these have been found to be less toxic to the cells than tungsten particles.

Techniques for coating the particles with DNA and bombarding plant and other cells are well known to those skilled in the art and are described in publications such as Sanford, 1993.

A further aspect of the invention includes a method for in vitro regeneration of a node segment of a plant to form a new transgenic plantlet, and comprises the steps of providing a node segment from a stem of a plant, introducing a foreign genetic material into a regenerable cell of the node segment, and culturing the node segment in a culture medium that does not contain callus-inducing hormones and, therefore, does not induce the formation of callus. Transfer of the node segment explants from the bombardment medium to regenerating culture medium may occur at any time after bombardment. For turfgrasses, transfer preferably occurs about 2–5 days after bombardment.

The regenerating culture medium may be the same or different than the culture/bombardment medium described above. The regenerating culture medium may contain shooting hormones and may additionally contain rooting hormones. A shooting hormone is a class of compounds known as cytokinins which includes synthetic shooting hormones, such as 6-benzyl-aminopurine (BAP), kinetin, zeatin, 2iP (Nβ(Δ²-isopentenyl)-adenine trans-6-(4-hydroxy-3-methylbut-2-enyl) amino purine. A rooting hormone is a class of compounds known as auxins which include indoleacetic acid, naphthaleneacetic acid and indolebutyric acid.

It has been found that certain turfgrass species, such as St. Augustinegrass, do not require a culture medium containing shooting and/or rooting hormones in order to form shoots from node segments. Therefore, for regeneration of these turfgrasses, culture medium that does not contain these hormones is preferred. A preferred medium for regeneration of node segments of turfgrasses is MS basal medium without 2,4-D, 3% sucrose, and a chemical used for selection of transgenic plants (e.g. 1 mg/L bialaphos to select for transient expression of the gene conferring resistance to a herbicide, such as Herbiace™).

Healthy shoots from presumptive transgenic explants growing in the presence of the selection chemical are then rooted and transferred to a medium (in the absence of biologically active hormones), such as soil or potting mix.

The above conditions lead to regeneration of green plantlets and plants with photosynthetic ability. As described above, a test used for confirmation that the gene is stably integrated into the genome of the host plant necessarily depends on the property to be conferred to the plant. For example, when the property is herbicide resistance, confirmation may be achieved by treatment of the growing plants by spraying or painting the leaves with the herbicide in a concentration that is lethal for control plants that have not been subjected to the transformation process.

The invention also extends to transgenic plants produced by the methods of the invention and node segments, embryo cells, callus cells, protoplasts, leaves, meristems, fruit, vegetables and seeds from the transgenic plants.

The following examples of the process for node segment transformation and regeneration of monocotyledonous plants are presented to further illustrate various embodiments of the present invention. These examples are not to be considered limiting, however, as other monocotyledons, transforming genes, plasmids, methods of transformation, culture media, and the like, may be used in the practice of the invention.

EXAMPLES

Biolistic Transformation of Node Segments and Regeneration of Transgenic St. Augustinegrass Plants St. Augustinegrass is a warm-season turfgrass used particularly for lawns in the southern United States. St. Augustinegrass is susceptible to a wide range of diseases, including dollar spot, brown patch, Helminthosporium spp., Fusarium blight, Fusarium patch, Pythium blight, red thread, stripe smut and Typhula blight. For these reasons, this grass species is an attractive target for biotechnology techniques. However, there have been no prior reports of transformation of St. Augustinegrass, or the regeneration of transgenic St. Augustinegrass plants.

Establishment of the Selection Conditions Plasmids Used for Bombardment

The constructs of the plasmids used for bombardment are illustrated in FIG. 4.

Examples 1–7

In these examples, node segments of mature commercial cultivars of St. Augustinegrass were transformed using a synthetic chimeric pat (bar) gene. The stable integration and expression of the pat gene renders the plant resistant to the herbicide, phosphinothricin. The plasmid used for transformation was pSAN41 which contains the pat gene under the control of the rice actin 1 (Act 1) promoter and a nopaline synthase (nos) 3' terminator. The Act 1 region is a ~1.3 kb fragment which contains the 5' flanking region, the site of transcription initiation, the first non-coding exon, the first intron and the start of the second exon of the rice gene.

Examples 8–13

In these examples, node segments of mature commercial cultivars of St. Augustinegrass were transformed using a chimeric CP4 gene. The stable integration and expression of the CP4 gene renders the plant resistant to the herbicide glyphosate, the active ingredient in the herbicide Roundup™. The plasmids used for transformation were (i) pMON25488, which contains the CP4 gene under the control of the 35S Cauliflower mosaic virus promoter with the rice actin intron and a nos 3' terminator, or (ii) plasmid pMON25496, which contains the 35S-CP4-nos 3' regions of pMON25488 and another CP4 gene under the control of the rice actin 1 (Act 1) promotor.

Harvesting and Preparation of Node Segments for Biolistic Bombardment

Young nodes were excised from mature greenhouse grown St. Augustinegrass plants (Cultivar 6-89-196, The Scotts Company, Marysville, Ohio.) and the leaves removed. Node segments (explants) of about 2 centimeters (cm) in length were sterilized with a solution of 10% Clorox and 0.075% (v/v) Tween-20 for 15 to 30 minutes, and then rinsed three times with sterile water. Tissues were trimmed from both ends of the explants, leaving less tissue above the node than below. One, two or three vertical cuts were made into the explants. Some explants did not receive cuts, but remained whole.

Plates were prepared for particle bombardment by placing approximately 10 nodal explants per Petri dish (cut end up, see FIG. 3) in MSA2D media alone (Murashige and Skoog medium containing 130 mg/L asparagine and 2 mg/L 2,4-dichlorophenoxyacetic acid), MSA2D media containing 0.1M mannitol and 0.1M sorbitol, or MSA2D media containing 0.3M mannitol and 0.3 M sorbitol. Uncut explants were stood on end in the Petri dishes. Plates were prepared 20 hours prior to bombardment and kept in the light.

Preparation of microprojectiles and DNA Samples and Biolistic Bombardment

In previous biolistic transformation experiments using creeping bentgrass, gold particles were found to be less toxic than tungsten particles. Therefore, gold particles were selected as microprojectiles for biolistic transformation of the St. Augustinegrass node segments. Gold particles were prepared by soaking at room temperature in 100% ethanol for 15 minutes, centrifuged briefly, washed 3 times in sterile, distilled water, and resuspended in water.

DNA samples consisting of 50 µl (5 mg) of the gold suspension, 5 µg plasmid construct DNA, 50 µl 2.5M $CaCl_2$ and 20 µl 0.1M spermidine were vortexed, centrifuged and resuspended in ethanol. The ethanol wash was repeated for a total of 3 times. The final pellet was resuspended in 30 μl ethanol, and 5 μl of the DNA solution was used per shot. Bombardment may be carried out utilizing any commercially available gene gun, such as those manufactured and sold by Bio-Rad Laboratories, Hercules, Calif. In the present examples, a prototype gene gun provided by Sanford Scientific, Inc., Waterloo, NY was employed at 1100 psi.

Selection After Bombardment

Three to five days after bombardment, the node segments were transferred to plates containing MS medium without hormones or osmoticum (MSO medium) but containing either 1 mg/L Herbiacel to select for shoots exhibiting transient expression of the pat (bar) gene or 0.1 mM glyphosate to select for transient expression of the CP4 gene. The MSO medium, without hormones, was used to prevent the formation of callus because it had been previously shown that shoots were not easily regenerated from callus cells of the St. Augustinegrass node segments.

Regenerating shoots from the selection plates were transferred to phytatray II (Sigma) for rooting once every month and transplanted to soil when the leaves were about 5–10 cm in length. About 2–3 weeks after transplanting to soil, when the plantlets are growing nicely, the plantlets are transferred to the greenhouse and treated with the respective herbicides, Herbiace™ or Roundup™, to select for stably transformed plantlets.

Herbicide rates are established by painting (with a paintbrush) untransformed control plants with different concentrations of the respective herbicide. Herbiace™ at 1.2 mg/ml was found to be lethal for control plants. Therefore, 1.6 mg/ml Herbiace™ was used to ensure that surviving plantlets were transgenic plants stably transformed with the pat gene. Herbicide rates for Roundup™ are established in a similar manner. The recommended concentration (1X) of Roundup™ for lethality for control plants is indicated on the Roundup™ label. To ensure that surviving plantlets are transgenic plants stably transformed with the CP4 gene, both control and presumptively transformed plantlets are treated with Roundup™ at three to five times (3X to 5X), preferably three times, the label-recommended lethal concentration.

The results of the transformations are illustrated in Table 1 and Table 2. Of 930 node segments bombarded with plasmid pSAN41, 26 plantlets were presumptively transformed for resistance to the herbicide, phosphinothricin and, of these, 2 plantlets were stably transformed with the pat gene for the herbicide resistance. Of 660 node segments bombarded with either plasmid pMON25488 or pMON25496, 28 plantlets were presumptively transformed for resistance to the herbicide, glyphosate. Each of these plantlets is then transferred to the greenhouse and treated with the herbicide Roundup™, as described above, to select for plantlets stably transgenic for the CP4 gene.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

TABLE 1

Transformation of St. Augustinegrass Node Segments With Pat Gene

| Example Number | Number of Plates Bombarded | Number of Node Segments Bombarded | Number of Plants Growing in Selection Medium | Number of Plants Surviving Herbicide Treatment |
|---|---|---|---|---|
| 1 | 9 | 90 | 1/1 plate | 1 |
| 2 | 18 | 180 | 4/2 plates | 1 |
| 3 | 18 | 180 | 15/9 plates | |
| 4 | 12 | 120 | 2/2 plates | |
| 5 | 12 | 120 | 4/3 plates | |
| 6 | 12 | 120 | 0 | |
| 7 | 12 | 120 | 0 | |

TABLE 2

Transformation of St. Augustinegrass Node Segments With CP4 Gene

| Example Number | Number of Plates Bombarded | Number of Node Segments Bombarded | Number of Plants Growing in Selection Medium |
|---|---|---|---|
| 8* | 12 | 120 | 0 |
| 9** | 12 | 120 | 0 |
| 10* | 12 | 120 | 0 |
| 11** | 12 | 120 | 0 |
| 12* | 12 | 120 | 6/4 plates |
| 13** | 6 | 60 | 22/6 plates |

*Bombarded with plasmid pMON25496.
**Bombarded with plasmid pMON25488.

PUBLICATIONS

Alexandrova, K. S., et al. (1996). Micropropagation of switchgrass by node culture. Crop Sci. 36: 1709–1711.

Darnell, J., H. Lodish, and D. Baltimore (1990). Molecular Cell Biology, Second Edition. Scientific American Books, Inc., pp.175–176.

Esau, Katherine (1965). Plant Anatomy, Second Edition. John Wiley & Sons, New York, p.73.

Hartman, C. L., Lee, L., Day, P. R., and N. E. Turner (1994). Herbicide resistant turfgrass (Agrostis palustris) by biolistic transformation. Bio/Technology 12: 919–923.

Klein, Theodore M., et al. (1988). Stable genetic transformation of intact Nicotiana cells by the particle bombardment process. PNAS 85: 8502–8505.

Kuo, Yu-Jen and M. A .L. Smith. (1993) Plant regeneration from St. Augustinegrass immature embryo-derived callus. Crop Sci. 33: 1394–1396.

Lee, Lisa. (1996). Turfgrass biotechnology. Plant Science 115: 1–8.

Pérez-Vicente, R., et al. (1993) Culture of vegetative and floral meristems in ryegrasses: potential targets for microballistic transformation. J. Plant Physiol. 142: 610–617.

Sanford, J. C., Smith, F. D., and J. A. Russell (1993). Optimizing the biolistic process for different biological applications. Methods in Enzymology 217: 483–509.

Serres R. A., et al. (1993). Particle-mediated transformation of perennial fruit plants capable of adventitious budding on micropropagated tissue. U.S. Pat. No. 5,240,839.

Tomes, Dwight T., et al. (1990). Transgenic tobacco plants and their progeny derived by microprojectile bombardment of tobacco leaves. Plant Molecular Biology 14: 261–268.

Tomes, Dwight, et al. (1991). Tissue culture method for transformation of plant cells. European Patent Application, EPO 0 424 047.

We claim:

1. A method for producing a transgenic turfgrass plant, comprising the steps of:
   providing a node segment from a stem of a turfgrass plant;
   inserting a foreign genetic material into the node segment to alter a physical, biochemical or physiological property of the node segment; and
   subjecting the node segment to culture conditions that do not induce callus formation and that select for regeneration of plantlets expressing the property, to permit direct regeneration of the node segment into a new transgenic turfgrass plant that expresses the property.

2. The method of claim 1, wherein the genetic material is inserted by microprojectile bombardment.

3. The method of claim 1, wherein the genetic material is inserted by Agrobacterium-mediated genetic transfer.

4. The method of claim 1, wherein the genetic material is inserted by direct DNA uptake mediated by electroporation.

5. The method of claim 1, wherein the node segment is provided from a plant that can be vegetatively propagated.

6. The method of claim 1, wherein the genetic material is inserted into the node segment within about 48 hours after providing the node segment from the plant.

7. The method of claim 1, wherein the culture conditions include culturing the node segment in a culture medium that does not include a shooting hormone.

8. A method for producing a transgenic turfgrass plant, comprising the steps of:
   providing a node segment from a stem of a turfgrass plant;
   inserting a foreign genetic material into a regenerable cell of the node segment followed by the stable integration of the genetic material into the genome of the cell, to produce a genetically transformed cell having an altered physical, biochemical or physiological property; and
   subjecting the node segment to culture conditions that do not induce callus formation and that select for regeneration of plantlets expressing the property, to permit direct regeneration of the transformed node segment cell into a new transgenic turfgrass plant that expresses the property.

9. A transformed cell from the node segment of claim 8.

10. The method of claim 1, wherein the turfgrass plant is selected from the group consisting of St. Augustinegrasses, bluegrasses, bentgrasses, bermudagrasses, buffalograsses, redtop, bahiagrasses, centipedegrass, zoysiagrasses, ryegrasses and fescues.

11. The method of claim 8, wherein the genetic material is inserted by microprojectile bombardment.

12. The method of claim 8, wherein the genetic material is inserted by Agrobacterium-mediated genetic transfer.

13. The method of claim 8, wherein the genetic material is inserted by direct DNA uptake mediated by electroporation.

14. The method of claim 8, wherein the turfgrass plant can be vegetatively propagated.

15. The method of claim 1, wherein the property is selected from the group consisting of herbicide resistance, disease resistance, insect resistance, drought resistance, dwarfism, improved nutrient utilization, antibiotic resistance, expression of a pigment, expression of a fragrance, improved nutritional content, increased production of seed, increased stress tolerance, expression of a regulatory gene to control indigenous genes, reduction of allergenic pollen production, and combinations thereof.

16. A transgenic St. Augustinegrass plant directly regenerated from a genetically transformed node segment of a St. Augustinegrass plant under culture conditions that do not induce the formation of callus, and having at least one altered physical, biochemical or physiological property compared to a St. Augustinegrass plant that is not transgenic for the property.

17. The transgenic St. Augustinegrass plant of claim 16, wherein the property is selected from the group consisting essentially of herbicide resistance, disease resistance, insect resistance, drought resistance, dwarfism, improved nutrient utilization, antibiotic resistance, expression of a pigment, expression of a fragrance, improved nutritional content, increased production of seed, increased production of fruit, increased stress tolerance, expression of a regulatory gene to control indigenous genes, reduction of allergenic pollen production, and combinations thereof.

18. A node segment from the transgenic plant of claim 16.

19. An embryo cell from the transgenic plant of claim 16.

20. A callus cell from the transgenic plant of claim 16.

21. A protoplast from the transgenic plant of claim 16.

22. A seed from the transgenic plant of claim 16.

23. A leaf from the transgenic plant of claim 16.

24. A meristem from the transgenic plant of claim 16.

25. The method of claim 1, wherein the culture conditions include culturing the node segment in a culture medium that does not include a rooting hormone.

26. The method of claim 1, wherein the culture conditions include culturing the node segment in a culture medium that does not include an osmoticum.

27. The method of claim 1, wherein the culture conditions include culturing in the light.

28. The method of claim 1, further comprising the step of placing a vertical cut in the node segment prior to inserting the foreign genetic material into the node segment cell.

29. The method of claim 1, wherein the transgenic turfgrass plant comprises a transgenic seed.

30. The method of claim 1, wherein the transgenic turfgrass plant comprises a transgenic embryo.

31. The method of claim 1, wherein the transgenic turfgrass plant comprises a transgenic callus cell.

32. The method of claim 1, wherein the transgenic turfgrass plant comprises a transgenic leaf cell.

33. The method of claim 1, wherein the transgenic turfgrass plant comprises a transgenic meristem.

34. The method of claim 1, further comprising isolating a transgenic protoplast from said transgenic plant.

35. The method of claim 1, wherein the transgenic turfgrass plant comprises a transgenic node segment.

36. The method of claim 10, wherein the transgenic turfgrass plant is St. Augustinegrass.

* * * * *